United States Patent [19]

Bloch et al.

[11] 4,039,793

[45] Aug. 2, 1977

[54] PRODUCTION OF MONOCHLORO- AND ARYL SUBSTITUTED SATURATED COMPOUNDS

[75] Inventors: Herman S. Bloch, Skokie; Louis Schmerling, Riverside, both of Ill.

[73] Assignee: UOP Inc., Des Plaines, Ill.

[21] Appl. No.: 607,311

[22] Filed: Aug. 25, 1975

Related U.S. Application Data

[63] Continuation-in-part of Ser. No. 507,086, Sept. 18, 1974, abandoned.

[51] Int. Cl.$^2$ .................. C07C 25/14; C07C 25/18; C07C 17/32
[52] U.S. Cl. .......................... 260/651 R; 260/649 R
[58] Field of Search............ 260/651 R, 649 R, 251 R

[56] References Cited

U.S. PATENT DOCUMENTS

| | | |
|---|---|---|
| 2,562,369 | 7/1951 | Schmerling ............... 260/648 R |
| 2,894,995 | 7/1959 | Schmerling ............... 260/650 R |
| 3,190,825 | 6/1965 | Huyser ..................... 260/651 R |

*Primary Examiner*—D. Horwitz
*Attorney, Agent, or Firm*—James R. Hoatson, Jr.; Kimbley L. Muller; William H. Page, II

[57] ABSTRACT

A process is disclosed for the production of monochloro- and aryl-substituted saturated compounds which comprises condensing an alkyl aromatic hydrocarbon containing from 1 to 10 carbon atoms in the alkyl substituent with a monochloromonoolefin possessing up to 14 carbon atoms and having the chlorine attached to one of the doubly-bonded carbon atoms in the presence of a free radical-generating catalyst.

11 Claims, No Drawings

PRODUCTION OF MONOCHLORO- AND ARYL SUBSTITUTED SATURATED COMPOUNDS

CLOSELY RELATED APPLICATIONS

This application is a continuation-in-part of our previously filed application Ser. No. 507,086 filed Sept. 18, 1974, now abandoned, all the teachings of which are specifically incorporated herein.

This invention relates to a process for the production of monochloro- and aryl-substituted saturated compounds. More specifically, this invention relates to a process for the production of monochloro- and aryl-substituted saturated compounds which comprises condensing an alkyl aromatic hydrocarbon containing from 1 to 10 carbon atoms in the alkyl substituent with a monochloromonoolefin possessing up to 14 carbon atoms and having the chlorine atom attached to one of the doubly-bonded carbon atoms in the presence of a free radical-generating catalyst.

The free radical-induced reaction of a saturated hydrocarbon with an unsaturated hydrocarbon is well known in the prior art. It is also well known in the prior art that an alkyl-substituted aromatic hydrocarbon may be condensed with a chloroolefin characterized by the presence of at least one chlorine atom on each of the doubly-bonded carbon atoms by means of free radical-generators.

In contradistinction to the prior art it has now been discovered that an alkyl aromatic hydrocarbon containing from about 1 to 10 carbon atoms in the alkyl substituent may also be condensed with a monochloromonoolefin in which the chlorine atom is attached to only one of the doubly-bonded carbon atoms, the condensation being induced by the presence of a free radical-generating catalyst, and in a preferred embodiment of this invention the condensation may also be enhanced by the added presence of a promoter comprising a hydrogen chloride compound. The utilization of the hereinbefore set forth hydrogen chloride embodiment will produce a greater percentage conversion of the original reactants, namely, the alkyl aromatic hydrocarbon and the monochloromonoolefin, and increase the percent yield of the monochloro- and aryl-substituted compound.

The desired products of the process of the present invention, namely, monochloro- and aryl-substituted saturated compounds, are utilized in the chemical industry in many ways. For example, various monochloro- and aryl-substituted saturated compounds may be converted to various aromatic diamino compounds which may be utilized in the chemical industry as antioxidants. It is also contemplated within the scope of the present invention that the monochloro- and aryl-substituted saturated compounds may also be utilized as a precursor for various chlorocontaining aromatic catalysts and catalyst modifiers such as arylsulfonic acids, aryl phosphines, and the like.

It is therefore an object of this invention to provide a process for the preparation of monochloro- and aryl-substituted saturated compounds.

A further object of this invention is to provide a process for the preparation of monochloro- and aryl-substituted saturated compounds utilizing a certain promoter composition of matter which will permit a more economical batch and continuous type operation.

In one aspect an embodiment of this invention resides in a process for the preparation of a mnochloro- and aryl-substituted saturated compound which comprises condensing an alkyl aromatic hydrocarbon containing from 1 to about 10 carbon atoms in the alkyl substituent with a monochloromonoolefin possessing up to about 14 carbon atoms and having the chlorine atom attached to one of the doublybonded carbon atoms in the presence of a free radical-generating catalyst at reaction conditions and recovering the resultant monochloro- and aryl-substituted saturated compound.

A specific embodiment of this invention resides in a process for the preparation of 1-chloro-3-phenylpropane which comprises condensing toluene with vinyl chloride at a temperature of from about 130° to 140° C. and a pressure of 1 atmosphere in the presence of concentrated hydrochloric acid, water and di-t-butyl peroxide to prepare the desired 1-chloro-3-phenylpropane.

A specific embodiment of this invention resides in a process for the preparation of 1-chloro-3-phenyl-3-methylbutane which comprises the condensation of isopropylbenzene with vinyl chloride in the presence of water and di-t-butyl perbenzoate at a temperature of 250° C. and a pressure of 1 atmosphere and recovering the resultant 1-chloro-3-phenyl-3-methylbutane.

Other objects and embodiments of the above set forth invention will be set forth in further detail in the following further discussion of the present invention.

As hereinbefore set forth, the present invention is concerned with a process for preparing monochloro- and aryl-substituted saturated compounds which comprises condensing an alkyl aromatic hydrocarbon containing from about 1 to about 10 carbon atoms in the alkyl substituent with a monochloromonoolefin possessing up to 14 carbon atoms and having the chlorine atom attached to one of the doubly-bonded carbon atoms in the presence of a free radical-generating catalyst and preferably in the presence of a promotor composition of matter comprising a hydrogen chloride compound.

The reaction is effected under conditions which include an elevated temperature of at least as high as the initial decomposition temperature of the free radical-generating catalyst. In addition, another reaction condition involves pressure, said pressure ranging from about atmospheric to about 100 atmospheres or more, however, the pressure is not a critical reaction parameter. When superatmospheric pressures are employed, said pressures are afforded by the introduction of vaporized reactants or a substantially inert gas such as nitrogen into the reaction zone. Another variable which is employed is the ratio of reactants, the alkyl-substituted aromatic hydrocarbon containing from 1 to 10 carbon atoms in the alkyl substituent usually being present in a mol ratio in a range of from about 1:1 up to about 10:1 mols per mol of monochloromonoolefin in which the chlorine atom is attached to one of the doubly-bonded carbon atoms.

Examples of suitable alkyl aromatic hydrocarbons containing from 1 to about 10 carbon atoms in the alkyl substituent will include any alkyl aromatic hydrocarbon, either monocyclic or polycyclic such as

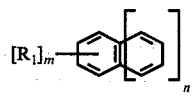

wherein $R_1$ is selected from alkyl substituents possessing from about 1 to about 10 carbon atoms and preferably is an alkyl radical containing at least one hydrogen atom attached to a carbon atom in an alpha position to the aromatic nucleus, m is an integer of at least 1 and no greater than 4 and n is an integer ranging from 0 to 5 and isomers thereof. Specific examples would include methylbenzene (also known as toluene), ethylbenzene, n-propylbenzene, isopropylbenzene, n-butylbenzene, isobutylbenzene, sec-butylbenzene, n-amylbenzene, sec-amylbenzene, isoamylbenzene, (2-methylbutyl)-benzene, n-hexylbenzene, n-heptylbenzene, n-octylbenzene, n-nonylbenzene, n-decylbenzene, hexylbenzene isomers, isoheptylbenzene isomers, octylbenzene isomers, nonylbenzene isomers, decyclbenzene isomers, o-xylene, m-xylene, p-xylene, pseudocumene, 1,2,3-trimethylbenzene, 1,3-diethylbenzene, 1,2-diethylbenzene, 1,4-diethylbenzene, 1,2-dipropylbenzene, 1,3-dipropylbenzene, 1,4-dipropylbenzene, diisopropylbenzenes, p-cymene, 1,2-dibutylbenzene, 1,3-dibutylbenzene, 1,4-dibutylbenzene, 1,2-diisoamylbenzene, 1,3-diisoamylbenzene, 1,4-diisoamylbenzene, 1,2-dihexylbenzene, 1,3-dihexylbenzene, 1,4-dihexylbenzene, 1,2,3-triheptylbenzene, 1,2,4-dihexylbenzene, 1,2,4-tri-n-octylbenzene, 1,3-dinonylbenzene, 1,2-didecylbenzene, 1,2-diisohexylbenzene, 1,2,3,4-tetramethylbenzene, 1,2,4,5-tetramethylbenzene (also known as durene), 1,2,3,4-tetraethylbenzene, 1,2,4,5-tetraethylbenzene, α-methylnaphthalene, α-ethylnaphthalene, α-propylnaphthalenes, α-butylnaphthalenes, α-amylnaphthalenes, α-hexylnaphthalenes, α-octylnaphthalenes, α-nonylnaphthalenes, α-decylnaphthalenes, β-methylnaphthalene, β-ethylnaphthalene, β-propylnaphthalenes, β-butylnaphthalenes, β-amylnaphthalenes, β-hexylnaphthalenes, β-octylnaphthalenes, β-nonylnaphthalenes, β-decylnaphthalenes, 1,3-dimethylnaphthalene, 1,4-dihexylnaphthalenes, 1,3-didecylnaphthalenes, 1-methylanthracene, 1-methylphenanthrene, 2-isopropylanthracene, 1-propylnaphthacene, 2-isononylnaphthacene, etc., 1-propylchrysene, 2-isononylchrysene, 1-amylpyrene, 2-isohexylpyrene, etc.

Suitable monochloromonoolefins which may be condensed with the aforementioned alkyl-substituted aromatic hydrocarbons containing from 1 to about 10 carbon atoms in the alkyl substituent will include monochloromonoolefins in which the chlorine atom is attached to one of the doubly-bonded carbon atoms, including non-cyclic and cyclic olefins. Such monochloromonoolefins will include vinyl chloride, in particular, and 1-chloropropene-1, 2-chloropropene-1, 1-chlorobutene-1, 2-chlorobutene-1, 1-chloropentene-1, 1-chlorohexene-1, 2-chlorohexene-1, 3-chlorohexene-3, 1-chloroheptene-1, 2-chloroheptene-1, 1-chlorooctene-1, 1-chlorononene-1, 1-chlorodecene-1, 1-chloroundecene-1, 2-chlorodecene-2, 3-chlorodecene-3, 1-chlorododecene-1, 1-chlorotridecene-1, 1-chlorotetradecene-1, 7-chlorotetradecene-7, 2-methyl-1-chlorobutene-1, 3,5,6-trimethyl-1-chloroheptene-1, 1-chlorocyclopentene-1, 1-chloro-2-methylcyclopentene-1, 1-chlorocyclohexene-1, 1-chlorocycloheptene-1, 1-chlorocyclooctene-1, etc.

The catalytic compositions of matter which are used in the process of the present invention comprise organic peroxides which are designated as free radical-generating catalysts. Examples of these catalysts which may be used include, in particular, the disubstituted hydrogen peroxides such as di-t-butyl peroxide, t-butyl perbenzoate, benzoyl peroxide etc. It is also contemplated within the scope of this invention that hydroperoxides such as acetyl hydroperoxide and t-butyl hydroperoxide may also be used although not necessarily with equivalent results.

The particular catalytic composition of matter chosen in the process of the present invention has an effect upon reaction temperature in that the reaction temperatures should be at least as high as the initial decomposition temperature of the free radical-generating catalysts, such as the peroxide compound, in order to liberate and form free radicals which promote the reaction. In selecting the particular reaction temperature for use in the process of the present invention two considerations must be taken into account. First, sufficient energy by means of heat must be supplied to the reaction system so that reactants, namely, the alkyl aromatic hydrocarbon containing from 1 to 10 carbon atoms in the alkyl substituent and the monochloromonoolefin in which the chlorine is attached to one of the doubly-bonded carbon atoms, will be activated sufficiently for condensation to take place when free radicals are generated by the catalyst. Second, free radical-generating catalysts such as the peroxy compounds, particularly organic peroxides, decompose at a measurable rate with time in a logarithmic function dependent upon temperature. The rate of decomposition can be, and ordinarily is, expressed as the half-life of the peroxide at a particular temperature. For example, the half-life in hours of di-t-butyl peroxide is 17.5 hours at 125° C., 5.3 hours at 135° C., and 1.7 hours at 145° C. (calculated from data for the first 33% decomposition). A reaction system temperature can be selected so that the free radical-generating catalyst decomposes smoothly with the generation of free radicals at a half-life which is not too long. In other words, sufficient free radicals must be present to induce the present chain reaction to take place, and these radicals must be formed at a temperature at which the reactants are in a suitably activated state for condensation. When the half-life of the free radical-generating catalyst is greater than about 10 hours, radicals are not generated at a sufficient rate to cause a reaction of the process of the present invention to go forward at a practical rate. Thus, the reaction temperature may be within the range of from about 50° C. to about 300° C. and at least as high as the decomposition temperature of the catalyst, by which is meant a temperature such that the half-life of the free radical-generating catalyst is not greater than 10 hours. Since the half-life for each free radical-generating catalyst is different at different temperatures, the exact temperature to be utilized in a particular reaction will vary. However, persons skilled in the art are well acquainted with the half-life versus the temperature data for different free radical-generating catalysts. Thus it is within the skill of one familiar with the art to select a particular temperature needed for any particular catalyst. However, the operating temperatures generally do not exceed the decomposition temperature of the catalyst by more than about 150° C. since free radical-generating catalysts decompose rapidly under such conditions. For example, when a free radical-generating catalyst such as t-butyl perbenzoate is used having a decomposition temperature of approximately 115° C. the process is run at a temperature ranging from 115° C. to about 265° C. When di-t-butyl peroxide having a decomposition temperature of about 130° C. is used, the process is run at a temperature ranging from 130° C. to about 280° C. Higher reaction temperatures may be employed, but little advantage is gained if the temperature is more than the hereinbefore mentioned 150° C. higher than the decomposition temperature of the catalyst. The general effect of increasing the operating temperature is to accelerate the rate of condensation reaction between the monochloromonoolefin in which the chlorine atom is attached to one of the doubly-bonded carbon atoms and the alkyl aromatic hydrocarbon containing from 1 to 10 carbon atoms in the alkyl substituent. However, the increased rate of reaction may be accompanied by a certain amount of undesired side reactions such as polymerization of the monochloromonoolefin.

It is contemplated within the scope of the present invention that a promoter comprising a hydrogen chloride compound will enhance the quantity of monochloro- and aryl-substituted saturated compound produced in the reaction. By "hydrogen chloride compound" is meant either anhydrous hydrogen chloride or aqueous hydrochloric acid. The effect upon the mechanism of the hereinbefore set forth reaction is that of increasing the yield of the monochloro- and aryl-substituted product. The mechanism of the action of the hydrogen chloride (which exhibits a marked and unique effect on free-radical induced reactions) is shown by the following example:

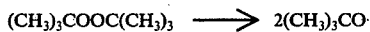

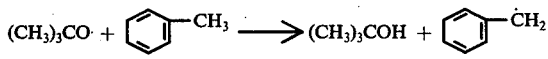

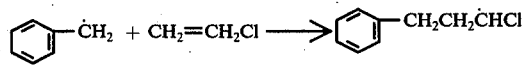

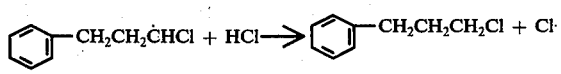

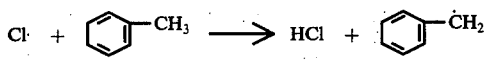

The so-formed benzyl radical starts a new cycle and 1-chloro-3-phenylpropane is produced by the resulting chain reaction. In the absence of hydrogen chloride, the following chain reaction occurs:

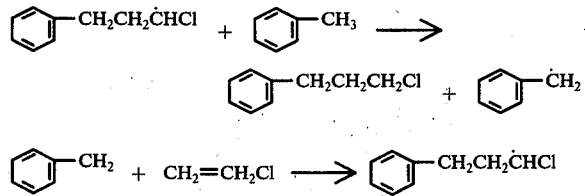

the 1-chloro-3-phenylpropyl radical abstracts a hydrogen atom more rapidly from hydrogen chloride than from toluene and therefore 1-chloro-3-phenylpropane is formed more rapidly (and hence in higher yield) than in the presence of hydrogen chloride. The desired compound is then formed before the monochloromonoolefin or the 1-chloro3-phenylpropyl radical undergo polymerization or other side reactions.

It is understood that the aforementioned alkyl aromatic hydrocarbons containing from 1 to about 10 carbon atoms, monochloromonoolefins in which the chlorine atom is attached to one of the doubly-bonded carbon atoms, and free radical-generating catalysts, are only representative of the class of compounds which may be employed and that the present invention is not necessarily limited thereto.

The process of this invention may be effected in any suitable manner and may comprise either a batch or a continuous operation. For example, when a batch type operation is employed, the reactants comprising the alkyl aromatic hydrocarbon containing from 1 to about 10 carbon atoms and the monochloromonoolefin in which the chlorine atom is attached to one of the doubly-bonded carbon atoms are placed in an appropriate apparatus along with a free radical-generating catalyst which may have a promoter comprising a hydrogen chloride compound added thereto. If atmospheric pressure is to be employed, the reaction vessel is then heated to a predetermined operating temperature. After maintaining the reactants in the reaction vessel at this temperature (suitably under reflux conditions) for a period of time which may range from 0.5 up to about 30 hours or more in duration, the heating is discontinued and the vessel is allowed to return to room temperature. The reaction mixture is then recovered, separated from the catalyst and the promoter and subjected to conventional means of purification and separation, said means including washing, drying, extraction, evaporation, fractional distillation, etc., whereby the desired monocyloro- and aryl-substituted saturated compound is recovered. Alternatively, if superatmospheric pressures are to be employed in the reaction, the reactants are charged to a pressure valve such as a rotating autoclave which contains a free radical-generating catalyst to which a promoter comprising a hydrogen chloride compound may have been added if it is desired in the reaction. The autoclave is sealed and a substantially inert gas such as nitrogen or helium is pressed in until the desired operating pressure is reached. The autoclave is then heated to the desired operating temperature and maintained thereat for a predetermined residence time. At the end of this time heating is discontinued, the autoclave is allowed to return to room temperature and the excess pressure is discharged. The autoclave is opened and the reaction mixture is then treated in a manner similar to that hereinbefore set forth whereby the desired monochloro- and aryl-substituted saturated compounds are separated and recovered.

It is also contemplated within the scope of this invention that the reaction process for obtaining a monochloro- and aryl-substituted saturated compound may be effected in a continuous manner of operation. When such a type of process is employed, the reactants comprising the alkyl aromatic hydrocarbon containing from 1 to 10 carbon atoms and the monochloromonoolefin in which the chlorine is attached to one of the doubly-bonded carbon atoms are continuously charged to the reaction vessel under conditions of good mixing as are the free radical-generating catalyst and the promoter comprising a hydrogen chloride compound, if used: the reactants and the catalysts and the promoter may be added from the same or from different inlet lines. After completion of the desired residence time, the reactor effluent is continually withdrawn and subjected to a conventional means of separation whereby the desired monochloro- and aryl-substituted saturated compounds are recovered, while any unreacted starting material comprising the alkyl aromatic hydrocarbon or the monochloromonoolefin are recycled to the reaction zone to form a portion of the feedstock.

The resultant products of this invention, the monochloro- and aryl-substituted saturated compounds, may be defined as saturated compounds which possess two substituents on the carbon atoms chains of the saturated compounds. The first substituent is a single chlorine atom and the second an aromatic radical. The term is not to be confused to be read as two separate substituted saturated compounds, but as one doubly substituted saturated compound. Specific examples of monochloro- and aryl-substituted saturated compounds would include 1-chloro-3-phenylpropane, 3-chloro-1-phenylheptane, 3-chloro-1-phenylpentane, 1-chloro-3-phenylbutane, 3-chloromethyl-4-phenylhexane, 4-chloro-5-benzyloctane, 1-chloro-3-p-tolylpropane, 1-chloro-3-o-tolyl-3-methylbutane, 1-chloro-3-α-naphthylpropane, 1-chloro-3-(9-anthryl)propane, 1-chloro-3-naphthacylpentane, etc. It is to be further understood that the aforementioned monochloro- and aryl-substituted saturated compounds are only representative of the class of compounds which may be prepared and that the present invention is not necessarily limited thereto.

The following examples which are given to illustrate the process of the present invention are not, however, intended to limit the generally broad scope of the present invention in strict accordance therewith.

EXAMPLE I

In this example 89.0 grams of toluene, 35.0 grams of vinyl chloride 20.0 grams of concentrated hydrochloric acid, 20.0 grams of water and 6.0 grams of di-t-butyl peroxide were mixed in a rotating 850-ml glass-lined rotating autoclave at a temperature of 130° C. to 140° C. at an initial pressure of 30 atmospheres of nitrogen for a period of time comprising 4 hours. At the end of this period of time the rotating autoclave was brought to conditions of ambient temperature by termination of heat to the autoclave and then to ambient pressure by means of a venting procedure. The reaction product was separated from the reaction vessel and any unreacted reactants and the residue (18.0 grams) were analyzed by means of gas-liquid chromatographic and infrared spectroscopy instrumentation. The chromatography disclosed four major peaks, the chief peak being shown by infrared analysis to be 1-chloro-3-phenylpropane which was formed by chloroethylation at the aliphatic (benzylic) carbon atom of the toluene.

EXAMPLE II

In this example 120 grams of isopropylbenzene, 30 grams of vinyl chloride, and 6 grams of t-butyl perbenzoate are heated in an 850-ml rotating autoclave under 30 atmospheres initial nitrogen pressure for a period of time comprising 5 hours at a temperature of 110°–115° C. The rotation autoclave is cooled to ambient temperature by means of the termination of heat to said autoclave. After cooling the reaction product and releasing its gaseous content, the product is removed from the autoclave and analyzed by gas-liquid chromatography and infrared spectroscopy instrumentation, said analysis disclosing the primary product to be 1-chloro-3-phenyl-3:methylbutane.

EXAMPLE III

In this example 120 grams of n-propylbenzene, 30 grams of vinyl chloride, 10 grams of concentrated hydrochloric acid, 10 grams of water and 6 grams of t-butyl perbenzoate are mixed in an 850-ml rotating autoclave for a period of time comprising 3 hours at a temperature of 120° C. and an initial nitrogen pressure of 30 atmospheres. The rotating autoclave is cooled to ambient temperature by means of the termination of the heat to said autoclave and allowed to return to ambient pressure by means of a venting procedure. After cooling and depressurizing the autoclave the reactant product is removed from the autoclave and analyzed by gas-liquid chromatography and infrared spectroscopy instrumentation, said analysis disclosing the primary product to be 1-chloro-3-phenylpentane.

EXAMPLE IV

In this example 125 grams of n-butylbenzene, 25 grams of 1-chloropentane-1 and 6 grams of di-t-butyl peroxide are mixed in an 850-ml rotating autoclave for a period of time comprising 3 hours at a temperature of 130°–140° C. and an initial nitrogen pressure of 5 atmospheres. The rotating autoclave is cooled and depressurized by termination of the heat to said autoclave and a venting procedure. After cooling and depressurizing the autoclave, the reaction product is removed and analyzed by the various analytical tools set forth in Examples I through III above. The analysis discloses the primary product to be 4-chloromethyl-5-phenyloctane.

The above set forth experiment is repeated substituting isobutylbenzene for the n-butylbenzene and 1-chlorotetradecene-1 for the 1-chloropentene-1. The final analysis discloses the product to be predominantly 4-chloromethyl-3-phenyl-2-methylhexadecane.

We claim as our invention:

1. A process for producing monochloro- and aryl-substituted saturated compounds which comprises condensing an alkyl aromatic hydrocarbon containing from 1 to about 10 carbon atoms in the alkyl substituent with a monochloromonoolefin possessing up to 14 carbon atoms and having the chlorine atom attached to one of the doubly-bonded carbon atoms in the presence of a free radical-generating catalyst at a temperature at least as high as the decomposition temperature of the free radical catalyst and a pressure of from about 1 atmosphere to about 100 atmospheres and recovering the resultant monochloro- and aryl-substituted saturated compound.

2. The process of claim 1 further characterized in that the free radical-generating catalyst is a peroxy compound.

3. The process of claim 2 further characterized in that the peroxy compound is di-t-butyl peroxide.

4. The process of claimm 1 further characterized in that the reaction is effected in the presence of a promoter comprising hydrogen chloride.

5. The process of claim 4 further characterized in that the hydrogen chloride is anhydrous.

6. The process of claim 4 further characterized in that the hydrogen chloride is aqueous.

7. The process of claim 1 further characterized in that the alkyl aromatic hydrocarbon is toluene, the monochloromonoolefin is vinyl chloride and the monochloro- and aryl-substituted saturated compound is 1-chloro-3-phenylpropane.

8. The process of claim 1 further characterized in that the alkyl aromatic hydrocarbon is n-pentylbenzene, the monochloromonoolefin is vinyl chloride and the monochloro- and aryl-substituted saturated compound is 1-chloro-3-phenylheptane.

9. The process of claim 1 further characterized in that the alkyl aromatic hydrocarbon is isopropylbenzene, the monochloromonoolefin is vinyl chloride and the monochloro- and aryl-substituted saturated compound is 1-chloro-3-phenyl-3-methylbutane.

10. The process of claim 1 further characterized in that the alkyl aromatic hydrocarbon is n-butylbenzene, the monochloromonoolefin is 1-chloropentene-1 and the monochloro- and aryl-substituted saturated compound is 4-chloromethyl-5-phenyloctane.

11. The process of claim 1 further characterized in that the alkyl aromatic hydrocarbon is isobutylbenzene, the monochloromonoolefin is 1-chlorotetradecene-1 and the monochloro- and aryl-substituted saturated compound is 4-chloromethyl-3-phenyl-2-methylhexadecane.

* * * * *